(12) United States Patent
Minai et al.

(10) Patent No.: US 7,536,217 B2
(45) Date of Patent: May 19, 2009

(54) SYSTEM FOR DETECTING POSITION OF CAPSULE ENDOSCOPE IN SUBJECT

(75) Inventors: Tetsuo Minai, Tokyo (JP); Hatsuo Shimizu, Tokyo (JP)

(73) Assignee: Olympus Corporation, Tokyo (JP)

( * ) Notice: Subject to any disclaimer, the term of this patent is extended or adjusted under 35 U.S.C. 154(b) by 581 days.

(21) Appl. No.: 11/017,499

(22) Filed: Dec. 20, 2004

(65) Prior Publication Data

US 2005/0143647 A1 Jun. 30, 2005

(30) Foreign Application Priority Data

Dec. 25, 2003 (JP) ............................. 2003-430404

(51) Int. Cl.
*A61B 5/05* (2006.01)
*A61B 6/00* (2006.01)
(52) U.S. Cl. ...................... 600/424; 600/476
(58) Field of Classification Search ................ 600/407, 600/410, 424; 128/899
See application file for complete search history.

(56) References Cited

U.S. PATENT DOCUMENTS

| | | | |
|---|---|---|---|
| 4,622,644 A * | 11/1986 | Hansen | ........................ 702/153 |
| 5,425,382 A | 6/1995 | Golden et al. | |
| 5,482,008 A * | 1/1996 | Stafford et al. | .............. 119/174 |
| 5,592,939 A * | 1/1997 | Martinelli | .................... 600/424 |
| 5,681,260 A | 10/1997 | Ueda et al. | |
| 5,879,297 A * | 3/1999 | Haynor et al. | ............... 600/407 |
| 2002/0173718 A1* | 11/2002 | Frisch et al. | ................. 600/424 |
| 2003/0085994 A1* | 5/2003 | Fujita et al. | .................... 348/77 |
| 2004/0111011 A1* | 6/2004 | Uchiyama et al. | ........... 600/160 |

FOREIGN PATENT DOCUMENTS

| | | |
|---|---|---|
| EP | 1 260 176 A2 | 11/2002 |
| JP | H03-136636 | 6/1991 |
| JP | 2959723 | 7/1999 |
| JP | 2001-179700 | 7/2001 |
| JP | 2003-19111 | 1/2003 |
| JP | 2003-117004 | 4/2003 |

OTHER PUBLICATIONS

International PCT Patent Publication No. WO 95/08130, dated Mar. 23, 1995 (Abstract only).

* cited by examiner

*Primary Examiner*—Eric F Winakur
*Assistant Examiner*—Michael T Rozanski
(74) *Attorney, Agent, or Firm*—Scully, Scott, Murphy & Presser, P.C.

(57) ABSTRACT

A system is for detecting a position of a device. The device is swallowed, passes through a subject, and includes a magnetic field generator generating a constant magnetic field. The system also includes a position transducer including a magnetic detector and a position processor. The magnetic detector is disposed at a fixed relative position to the subject, and detects an intensity of a constant magnetic field output from the magnetic field generator. The position processor calculates a position of the device in the subject based on the intensity detected by the magnetic field intensity detector.

33 Claims, 10 Drawing Sheets

SYSTEM FOR DETECTING POSITION OF CAPSULE ENDOSCOPE IN SUBJECT

CROSS-REFERENCE TO RELATED APPLICATIONS

This application claims the benefit of priority of Japanese Patent Application No. 2003-430404 filed on Dec. 25, 2003, and the disclosure of which is incorporated herein by its entirety.

BACKGROUND OF THE INVENTION

1) Field of the Invention

The present invention relates to a system for detecting a position of a device such as a capsule endoscope, which is swallowed and passes naturally through the digestive tract of the subject, by a position transducer that is disposed on the outside of the subject and obtains information of the position of the device in the subject.

2) Description of the Related Art

In recent years, in the field of endoscopes, a swallowable capsule endoscope has been proposed. The capsule endoscope has an image capturing function and a radio communication function. The capsule endoscope has the function of traveling in the body cavity, for example, in the organs such as the stomach and the small intestine with peristalsis of the organs and sequentially capturing images for a period of time since the capsule endoscope is swallowed from the mouth of a subject for inspection (examination) until it is naturally excreted.

Image data captured in the body by the capsule endoscope as the capsule endoscope travels in the body cavity is sequentially transmitted by radio communication to the outside and stored into a memory provided on the outside. The subject can freely move throughout the period after he/she swallows the capsule endoscope until it is excreted by carrying a receiver having a radio communication function and a storing function. After the capsule endoscope is excreted, a doctor or nurse can display the images of the organs on a display based on the image data stored in the memory and make a check.

A capsule endoscope has been proposed in which the receiver has the function of detecting the position of the capsule endoscope in the subject to capture, for example, an endoscope image of a specific organ in the subject. As an example of a capsule endoscope system having the position detecting function, a capsule endoscope system using the radio communication function provided in the capsule endoscope is known. Specifically, the system has a configuration that a receiver provided on the outside of a subject has a plurality of antenna elements, and has the function of receiving a radio signal transmitted from the capsule endoscope by the plurality of antenna elements and, based on intensities received by the antenna elements, detecting the position of the capsule endoscope in the subject (see Japanese Patent Application Laid-open No. 2003-19111, for example).

SUMMARY OF THE INVENTION

It is an object of the present invention to at least solve the problems in the conventional technology.

A system according to one aspect of the present invention includes a device that is swallowed, passes through a subject, and includes a magnetic field generator generating a constant magnetic field; and a position transducer that includes a magnetic detector and a position processor. The magnetic detector is disposed at a fixed relative position to the subject, and detects an intensity of a constant magnetic field output from the magnetic field generator. The position processor calculates a position of the device in the subject based on the intensity detected by the magnetic field intensity detector.

The other objects, features, and advantages of the present invention are specifically set forth in or will become apparent from the following detailed description of the invention when read in conjunction with the accompanying drawings.

DETAILED DESCRIPTION

Exemplary embodiments of a system for detecting a position of a capsule endoscope in a subject relating to the present invention will be explained in detail below with reference to the accompanying drawings. It should be noted that the drawings are schematic ones and the relation between thickness and width of each part, the thickness ratio of the parts, and the like are different from real ones. Obviously, the drawings include parts having different relations of dimensions and ratios.

Figure 1:
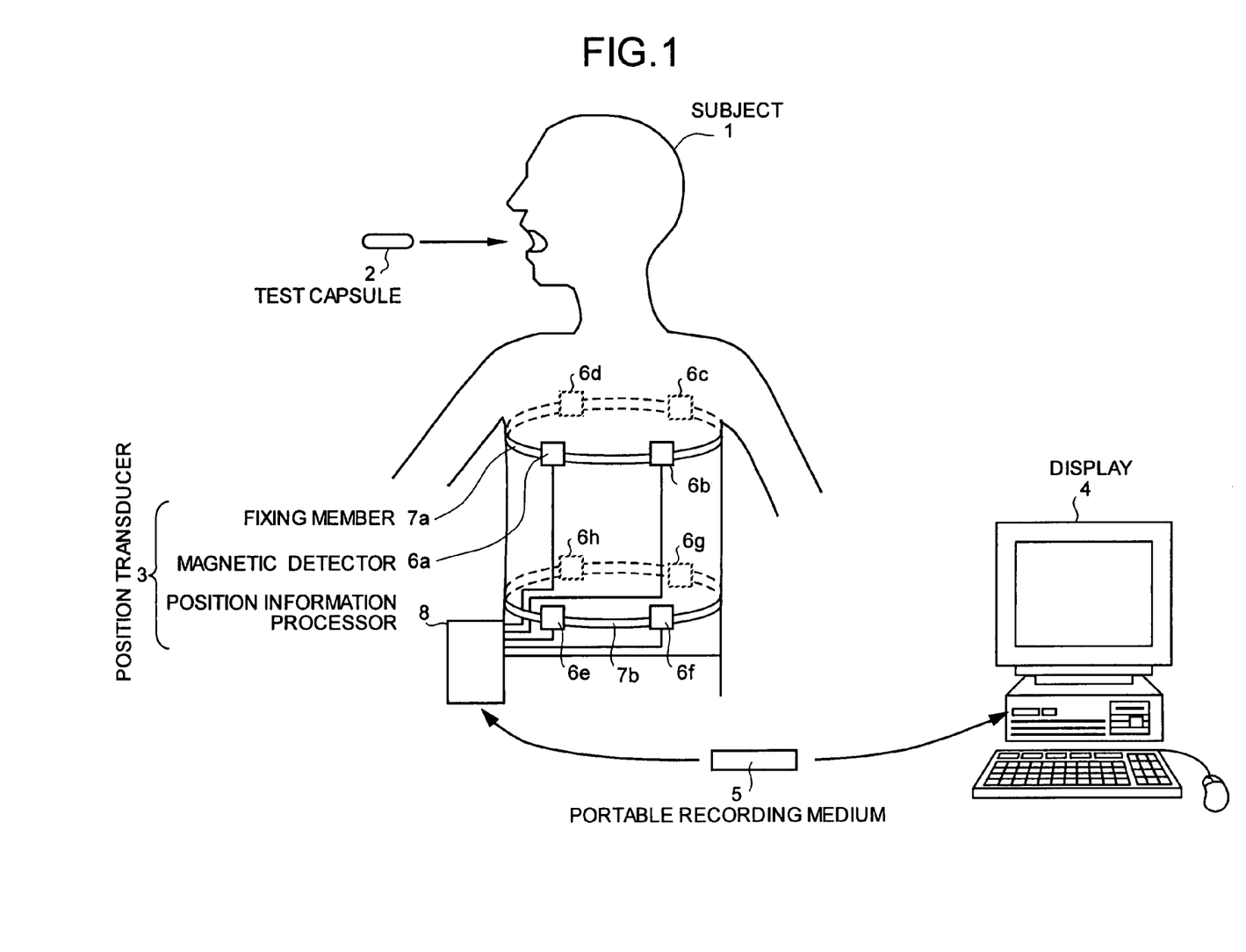
FIG. 1 is a schematic view of a system for detecting a position of a capsule endoscope in a subject according to a first embodiment.

A system for detecting a position of a capsule endoscope in a subject according to a first embodiment will now be explained. The system for detecting a position of a capsule endoscope according to the first embodiment of the present invention includes a test capsule 2 that is swallowed and passes though a subject 1 and functions as an example of a device to be traveled in a subject; a position transducer 3 that detects the position in the subject 1 of the test capsule 2; a display 4 displaying position information of the test capsule 2 detected by the position transducer 3; and a portable recording medium 5 for transmitting/receiving information between the position transducer 3 and the display 4.

The display 4 is used for displaying position information of the test capsule 2 obtained by the position transducer 3 and has a configuration like a workstation or the like that displays an image based on data obtained from the portable recording medium 5. Concretely, the display 4 may be constructed to directly display an image by a cathode-ray tube (CRT) display, a liquid crystal display, or the like or to output an image to another medium like a printer or the like.

The portable recording medium 5 can be inserted/removed to/from a position processor 8 that is explained later and the display 4, and has a structure capable of outputting and recording information when inserted to the position processor 8 and the display 4. Concretely, the portable recording medium 5 is inserted in the position processor 8 to record information on the position of the test capsule 2 while the test capsule 2 travels in the body cavity of the subject 1. After the test capsule 2 is excreted from the subject 1, the portable recording medium 5 is removed from the position processor 8 and inserted into the display 4, and the recorded data is read by the display 4: By transmitting data between the position processor 8 and the display 4 by the portable recording medium 5 such as a compact flash (trademark) memory, different from the case where the position processor 8 and the display 4 are connected to each other by wire, even when the test capsule 2 is traveling in the subject 1, the subject 1 can move freely.

The test capsule 2 is used at the time of conducting a preliminary inspection to check whether or not a narrow part in which passage of a capsule endoscope is difficult exists in the subject 1 before introduction of the capsule endoscope or the like into the subject 1. The system according to the first embodiment is used to check how the test capsule 2 travels in the subject 1. To achieve the purpose, a high-precision position detecting mechanism is provided.

Figure 2:
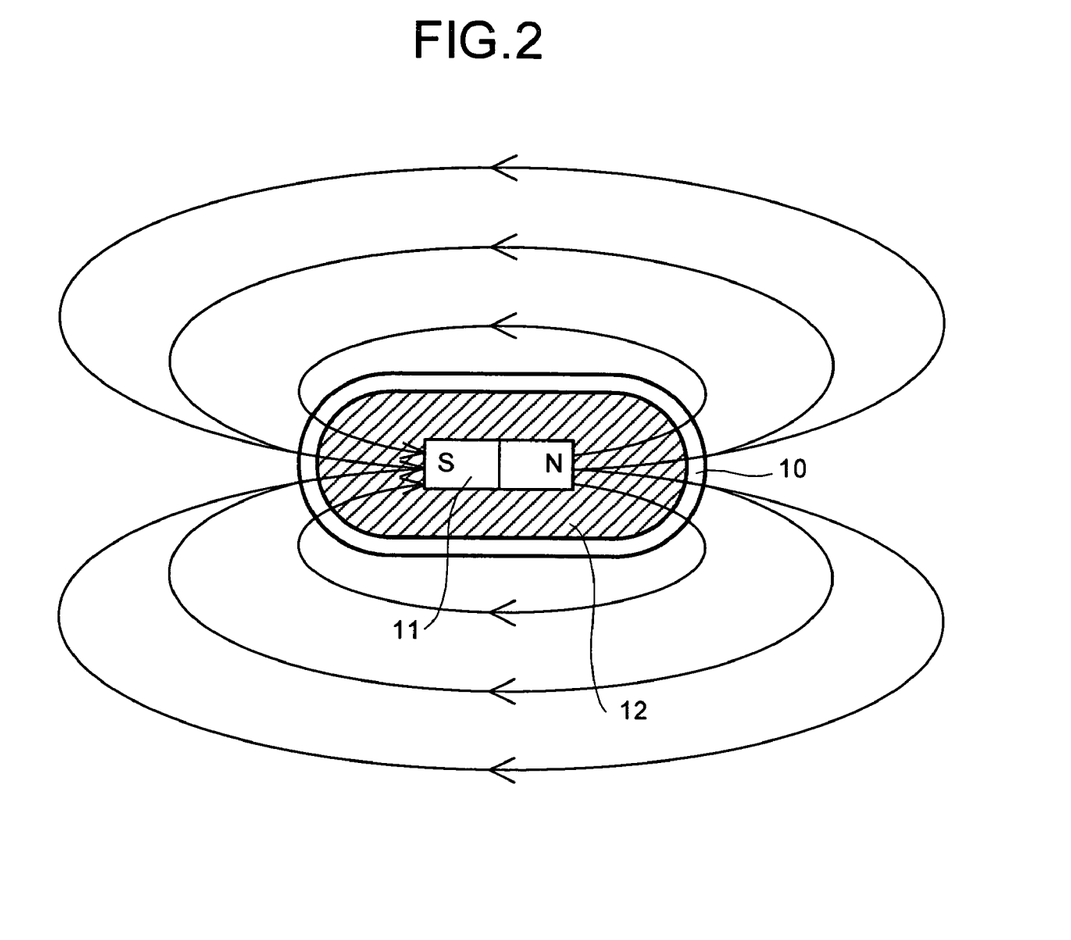
FIG. 2 is a schematic view of a test capsule as a component of the system according to the first embodiment.

FIG. 2 is a schematic diagram of the test capsule 2. As shown in FIG. 2, the test capsule 2 includes a casing 10 having a capsule shape that is similar to that of a casing of a capsule endoscope; a permanent magnet 11 disposed in the casing 10; and a filling member serving to fill the clearance between the inner surface of the casing 10 and the permanent magnet 11.

The casing 10 is made of, for example, a bio-compatible material and has a characteristic such that when the casing 10 remains in the subject 1 for a few days, the material dissolves. By forming the casing 10 of a bio-compatible material, there is an advantage such that even if the test capsule 2 introduced in the subject 1 is not excreted to the outside of the subject 1, it is unnecessary to perform an abdominal operation or the like on the subject 1.

The permanent magnet 11 functions as a magnetic field generator in the claims, has a size that can be housed in the casing 10, and is to output a constant magnetic field whose intensity fluctuation with time is ignorable. In place of the permanent magnet 11, for example, a coil that receives constant current and generates a constant magnetic field may be used as the magnetic field generator. In the case of using the permanent magnet 11, there is an advantage such that drive power is unnecessary. Thus, it is preferable to construct the magnetic field generator by using the permanent magnet 11.

As shown in FIG. 2, the constant magnetic field generated from the permanent magnet 11 is expressed by a line of magnetic force of a closed curve that is output from the N pole side, travels on the outside of the permanent magnet 11, and enters again on the S pole side. As shown in FIG. 2, the travel direction of the line of magnetic force has location dependency but it can be regarded that the intensity of the constant magnetic field expressed by the line of magnetic force is determined only in accordance with the distance from the test capsule 2. Specifically, the size of the permanent magnet 11 provided in the test capsule 2 is small enough to be ignored as compared with the distance between the test capsule 2 and magnetic detectors 6a to 6h. Consequently, magnetic field intensity P at a point apart from the test capsule 2 only by distance "r" is expressed as follows by using a proportional factor α.

$$P = \alpha/r^3 \qquad (1)$$

The system according to the first embodiment detects the position of the test capsule 2 based on the relation shown in Equation (1) as is explained later.

The filling member 12 is provided to fill the clearance between the inner face of the casing 10 and a permanent magnet 11 to fix the position of the permanent magnet 11. The material of the filling member 12 does not exert an adverse influence on the subject 1. For example, the filling member 12 is made of barium sulfate. Since barium sulfate can be used as a contrast medium in an X-ray inspection, position detection by an X-ray inspection can be performed in addition to the position detection of the first embodiment. By comparing the results of both of the inspections, more accurate position detection can be performed. Obviously, it is not essential to use barium sulfate as the filling member 12 in the first embodiment and an arbitrary material can be used as long as the material functions as the filling member.

The position transducer 3 is explained. The position transducer 3 detects the position of the test capsule 2 in the subject 1 based on the constant magnetic field output from the test capsule 2. Concretely, the position transducer 3 has, as shown in FIG. 1, the magnetic detectors 6a to 6h for detecting the intensity of the constant magnetic field output from the test capsule 2, a fixing member 7a for fixing the magnetic detectors 6a to 6d to the subject 1, a fixing member 7b for fixing the magnetic detectors 6e to 6h to the subject 1, and the position processor 8 for calculating the position of the test capsule 2 based on the magnetic field intensities detected by the magnetic detectors 6a to 6h.

Each of the magnetic detectors 6a to 6h is to detect the magnetic field intensity in the position where it is disposed. More specifically, each of the magnetic detectors 6a to 6h is constructed by a Magneto Impedance (MI) sensor, for example. The MI sensor has a configuration using, for example, an FeCoSiB amorphous wire as a magneto-sensitive medium and senses the magnetic field intensity by using an MI effect that the magnetic impedance of the magneto-sensitive medium largely changes according to an external magnetic field when high-frequency current is passed to the magneto-sensitive medium. The magnetic detectors 6a to 6h may be constructed by other magnetic sensors, though the MI sensor provides particularly highly sensitive magnetic intensity detection. In the first embodiment, the magnetic detectors 6a to 6h are disposed such that they are located at apexes of a cube.

The fixing members 7a and 7b fix the magnetic detectors 6a to 6h to the subject 1. Concretely, each of the fixing members 7a and 7b is formed, for example, of an elastic member in an annular shape and is fixed in a state where it is closely attached to the trunk of the subject 1. The magnetic detectors 6a to 6d and the magnetic detectors 6e to 6h are fixed to predetermined positions in the subject 1 by the fixing members 7a and 7b, respectively. By closely attaching the fixing members 7a and 7b to the trunk of the subject 1, the magnetic detectors 6a to 6h are disposed in a state where their relative positions to the subject 1 are fixed.

Figure 3:
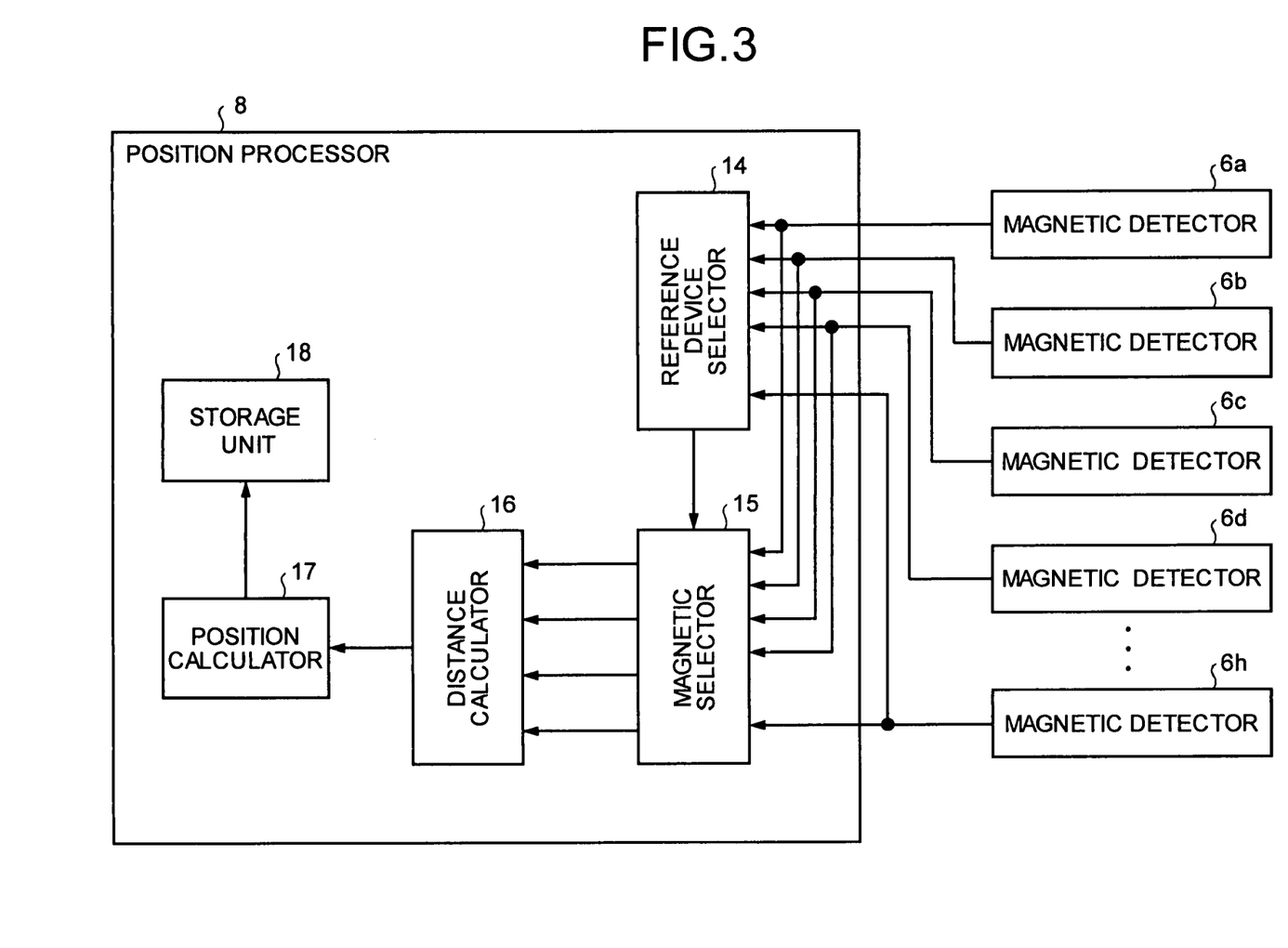
FIG. 3 is a schematic view of a position processor as a component of the system according to the first embodiment.

The position processor 8 calculates the position of the test capsule 2 based on the magnetic field intensities sensed by the magnetic detectors 6a to 6h. A concrete configuration of the position processor 8 is as shown in the block diagram of FIG. 3. As shown in FIG. 3, the position processor 8 includes a reference device selector 14 that selects a reference magnetic detector (hereinbelow, called "reference device") from the magnetic detectors 6a to 6h, and a magnetic selector 15 that outputs the magnetic field intensity obtained by the predetermined number of magnetic detectors based on the result of selection by the reference device selector 14. The position processor 8 includes a distance calculator 16 for calculating distance between the test capsule 2 and the reference device or the like based on the magnetic field intensity output from the magnetic selector 15; a position calculator 17 for calculating the position of the test capsule 2 by performing a computing process using the calculated distance and position coordinates of the reference device or the like used for calculating the distance; and a storage unit 18 for storing information of the position of the test capsule 2 obtained by the position calculator 17 into the portable recording medium 5.

The reference device selector 14 has the function of selecting the magnetic detector with the largest value of the detected magnetic field intensity from the magnetic detectors 6a to 6h. Concretely, the reference device selector 14 compares the magnetic field intensity values output from the magnetic detectors 6a to 6h with each other, selects the magnetic detector (reference device) that has output the largest magnetic field intensity value, and outputs information specifying the reference device (for example, information indicating the reference device among the magnetic detectors 6a to 6h) to the magnetic selector 15.

The magnetic selector 15 selects a plurality of magnetic detectors based on the result of selection of the reference device selector 14 and outputs the magnetic field intensities obtained by the selected magnetic detectors (selected devices) to the distance calculator 16. Concretely, the magnetic selector 15 has the function of selecting three magnetic detectors disposed in directions orthogonal to each other with respect to the reference device. Specifically, in the system according to the first embodiment, as also shown in FIG. 1, the magnetic detectors 6a to 6h are disposed so as to form vertexes of a cube, so that three magnetic detectors positioned in direction orthogonal to each other always exist for an arbitrary magnetic detector, and the magnetic selector 15 has the function of selecting the three magnetic detectors as selected devices.

The distance calculator 16 calculates the distances among the reference device, the selected devices, and the test capsule 2 based on the magnetic field intensities received via the magnetic selector 15. Concretely, the distance calculator 16 has the function of calculating the distance between the magnetic detector that has detected the magnetic field intensity and the test capsule 2 by performing the computing process shown by Equation (1) with respect to the input magnetic field intensity.

The position calculator 17 calculates the position of the test capsule 2 by performing a predetermined computing process based on the distance between the magnetic field intensity detecting device selected as a reference device or the like and the test capsule 2. The position calculator 17 also has the function of calculating the position of the test capsule 2 and, after that, outputting the result of calculation to the storage unit 18.

Figure 4:
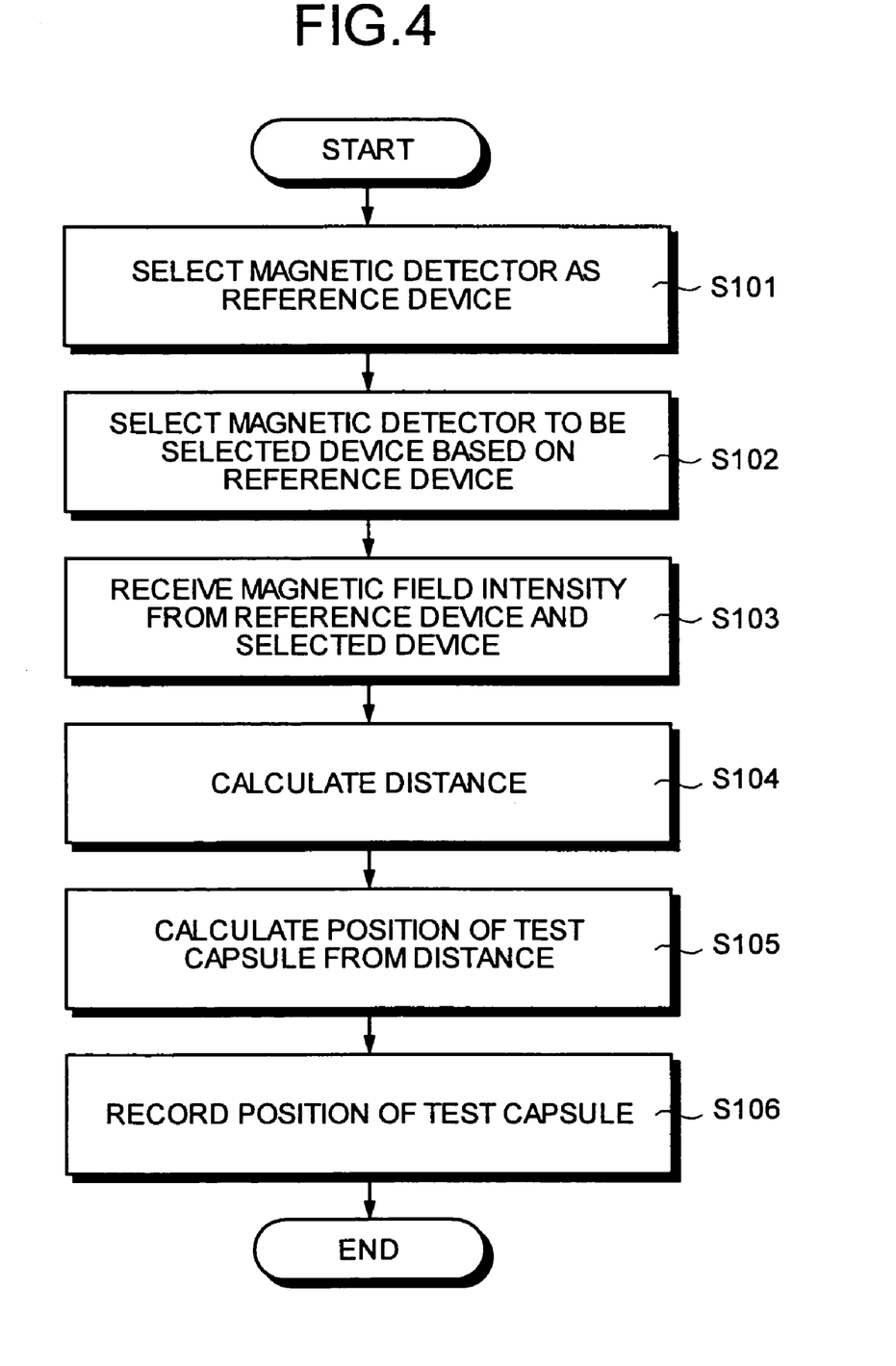
FIG. 4 is a flowchart of operations of the position processor.
Figure 5:
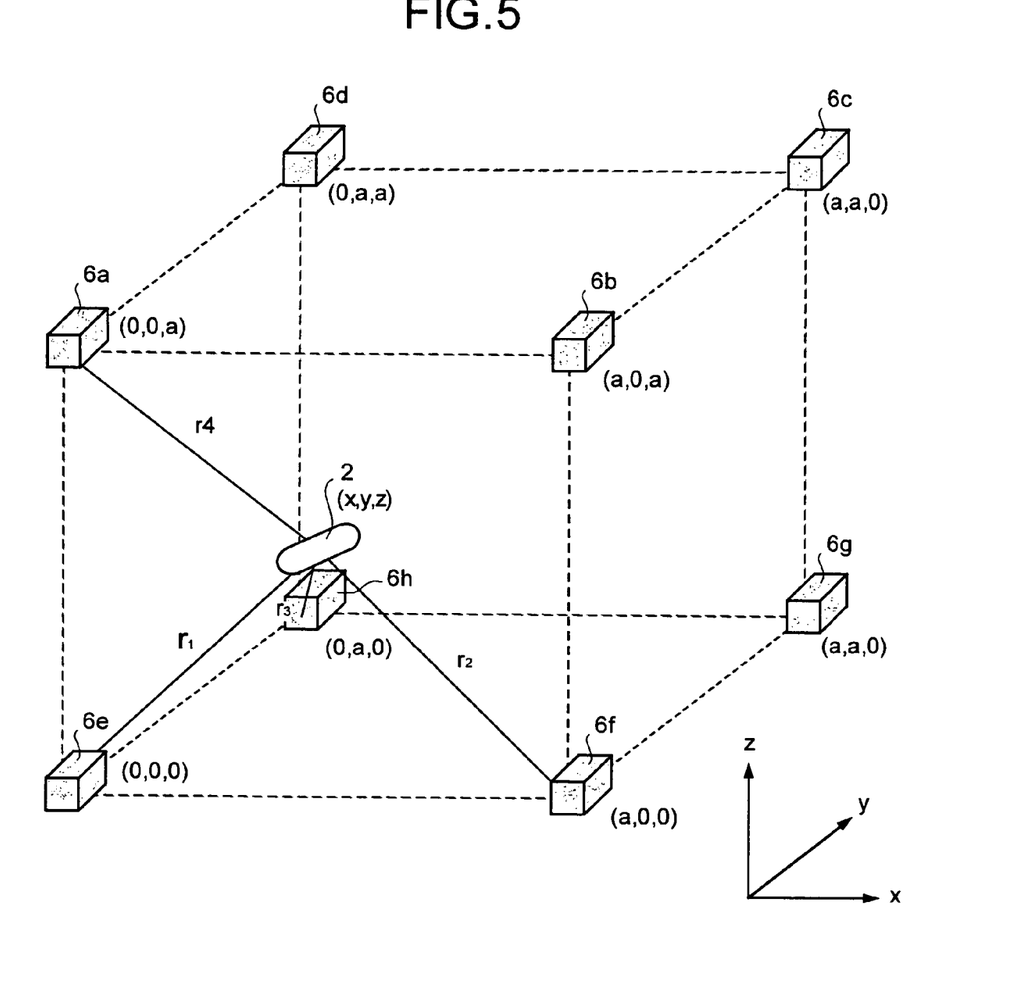
FIG. 5 is a schematic view of calculating the position of a test capsule by the position processor.

The operation of the position processor 8 in the first embodiment is explained. FIG. 4 is a flowchart that depicts the operation of the position processor 8, and FIG. 5 is a schematic diagram for explaining the algorithm of the position calculation. In FIG. 5, the length of one side of a cube constructed by the magnetic detectors 6a to 6h is set as "a". As is explained later, the position of the magnetic detector 6e selected as a reference device is set as the origin, the direction from the magnetic detector 6e toward the magnetic detector 6f is set as an x direction, the direction from the magnetic detector 6e toward the magnetic detector 6h is set as a y direction, and the direction from the magnetic detector 6e toward the magnetic detector 6a is set as a z direction. The positions of the magnetic detectors 6a to 6h are determined based on the xyz coordinate system, and the position of the test capsule 2 in the xyz coordinate system is expressed as (x,y,z). The operation of the position processor 8 is explained hereinbelow by properly referring to FIGS. 4 and 5.

First, the position processor 8, using the reference device selector 14, selects the magnetic detector having the magnetic field intensity that is the highest among the magnetic field intensities received by the magnetic detectors 6a to 6h (step S101). The example of FIG. 5 is a case where the magnetic detector 6e is selected as the magnetic detector sensing the highest magnetic field intensity. In the following description, it is also assumed that the magnetic detector 6e is the reference voltage.

The position processor 8 selects three devices by the magnetic selector 15 based on the reference device selected in step S101 (step S102), and outputs the magnetic field intensities obtained by the reference device and the selected devices to the distance calculator 16 (step S103). In the example of FIG. 5, the magnetic detectors 6f, 6h, and 6a are disposed in the directions orthogonal to each other with respect to the magnetic detector 6e as a reference device, so that the magnetic selector 15 selects the magnetic detectors 6f, 6h, and 6a as selected devices.

After that, the position processor 8 calculates the distance from the test capsule 2 based on the magnetic field intensity obtained by the reference device selected in step S101 and the magnetic field intensities obtained by the devices selected in step S102 by the distance calculator 16 (step S104). Concretely, the distance calculator 16 calculates the distance by performing computation of Equation (1) using the magnetic field intensity input via the magnetic selector 15. In the example of FIG. 5, the distance calculator 16 calculates distances $r_1$, $r_2$, $r_3$, and $r_4$ between the test capsule 2 and the magnetic detectors 6e, 6f, 6h, and 6a, respectively, based on the magnetic field intensities detected by the reference device and the selected devices.

The position processor 8 calculates the position of the test capsule 2 by the computing process in the position calculator 17 (step S105). Concretely, the position of the test capsule 2 is calculated by deriving the x coordinate, y coordinate, and z coordinate of the test capsule 2, so that the coordinates of the test capsule 2 are derived by using the coordinates of the magnetic detectors 6e, 6f, 6h, and 6a and the values of distances derived in step S104.

For example, the position coordinates (x,y,z) of the test capsule 2 can be geometrically derived from the positional relations shown in FIG. 5 and, concretely, can be calculated by solving the following equations.

$$(x-0)^2+(y-0)^2+(z-0)^2=r_1^2 \qquad (2)$$

$$(x-a)^2+(y-0)^2+(z-0)^2=r_2^2 \qquad (3)$$

$$(x-0)^2+(y-a)^2+(z-0)^2=r_3^2 \qquad (4)$$

$$(x-0)^2+(y-0)^2+(z-a)^2=r_4^2 \qquad (5)$$

In Equations (2) to (5), the number of unknown letters is three so that three equations are theoretically sufficient. At the time of actual position detection, however, to suppress deterioration in precision of the position detection of the test capsule 2 due to positional deviations of the magnetic detectors 6a to 6h, a distance derivation error, and the like, after solving Equations (2) to (5), the coordinates of the magnetic detector, and the like are corrected so that the values x, y, and z are unconditionally determined.

Finally, the position processor 8 stores the position of the test capsule 2 calculated in step S105 by the storage unit 18

(step S106). Concretely, while the test capsule 2 is swallowed in the subject 1, the portable recording medium 5 is inserted in the storage unit 18, so that the storage unit 18 records the position information obtained in step S105 into the portable recording medium 5.

The processes in steps S101 to S106 are repeatedly performed at predetermined time intervals. As a result, the portable recording medium 5 records information of travel in the subject 1 of the test capsule 2. After the test capsule 2 is excreted to the outside of the subject 1, the portable recording medium 5 is inserted to the display 4. The user grasps how the test capsule 2 travels in the subject 1 based on the result of recording displayed on the display 4 and determines the location of a narrow region existing in the subject 1 or the like from the grasped result.

The advantages of the system according to the first embodiment is explained. First, the system according to the first embodiment calculates the position of the test capsule 2 based on the constant magnetic field output from the permanent magnet 11 in the test capsule 2. Different from electromagnetic waves and the like, the constant magnetic field has a characteristic that its intensity attenuates almost unconditionally irrespective of physical parameters such as dielectric constant, magnetic permeability, and the like in a propagation region, so that the relation of Equation (1) is excellently satisfied. Therefore, the system has an advantage such that position detection can be performed with higher precision even in a space like the inside of a human body where organs and the like whose physical parameters are different from each other exist as compared with position detection using electromagnetic waves or the like.

Another advantage of using the constant magnetic field is that burden on the subject when the test capsule 2 is introduced into the subject 1 is lessened. For the above reasons, the system according to the first embodiment has an advantage such that deterioration in precision of the position detection due to variations of environments around the test capsule 2 is suppressed. Consequently, for example, at the time of introducing the test capsule 2 into the subject 1, it is unnecessary to impose limitations such as restriction on eating and drinking like in other inspecting methods. Therefore, the subject 1 can live normal life also at the time of an inspection using the test capsule 2 and the burden on the subject 1 in the inspection can be lessened.

Figure 6:
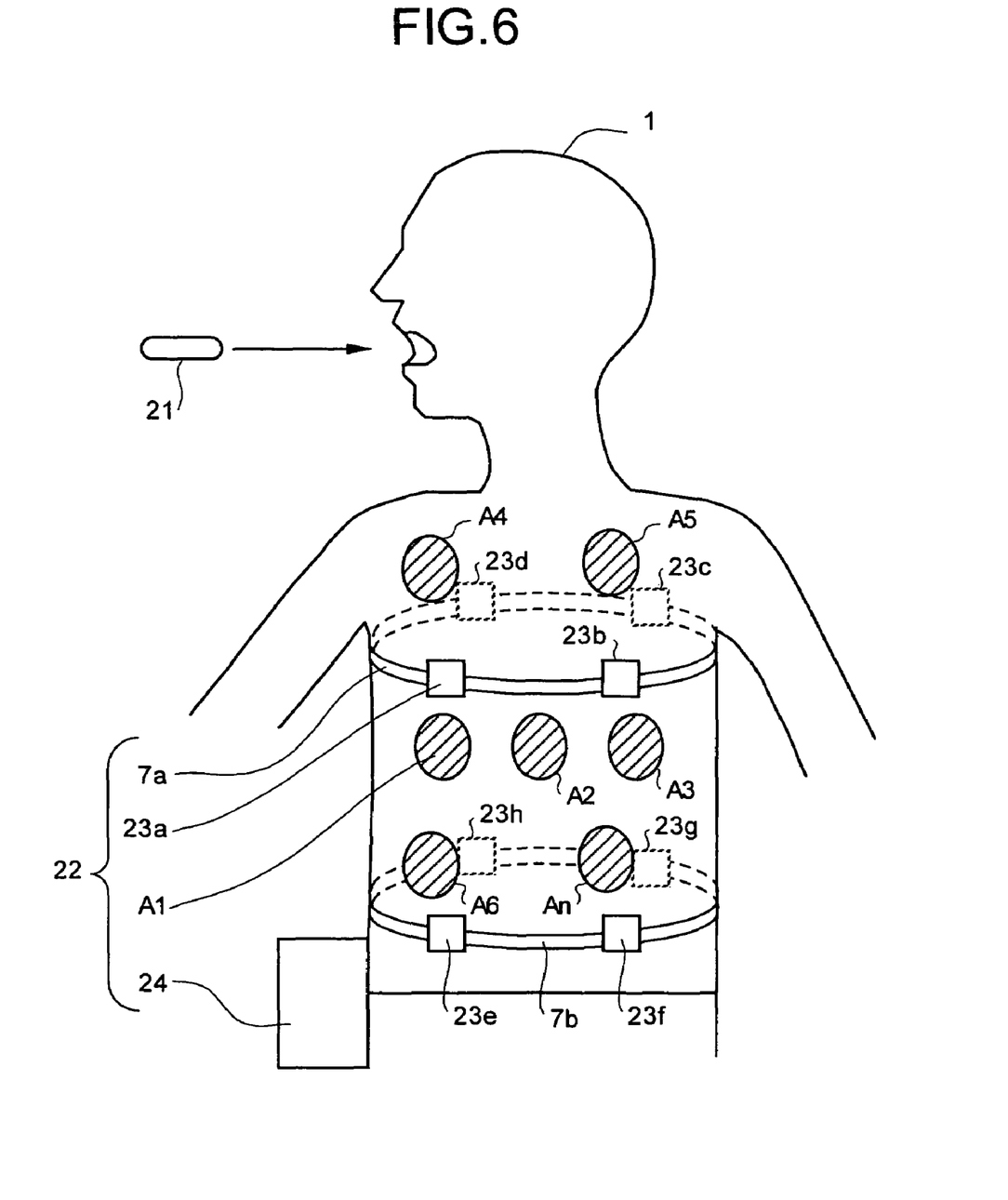
FIG. 6 is a schematic view of a system for detecting a position of a capsule endoscope in a subject according to a second embodiment.

A system for detecting a position of a capsule endoscope in a subject according to a second embodiment will now be explained. The system according to the second embodiment includes a capsule endoscope, as a device swallowed and passing through a subject, including not only the constant magnetic field generator but also a predetermined function executing unit and a radio unit; and a position processor for switching a plurality of antennas for receiving radio signals transmitted from the capsule endoscope based on the constant magnetic field generated by constant magnetic field generator and the result of detection of the position of the capsule endoscope in the subject as well as the direction of the longitudinal axis of the capsule endoscope, in other words, the orientation direction of the capsule endoscope.

FIG. 6 is a schematic diagram of the system according to the second embodiment. As shown in FIG. 6, the system according to the second embodiment includes a capsule endoscope 21 as an example of the device to be swallowed and passes through a subject, and a position transducer 22. Although elements corresponding to the display 4 and the portable recording medium 5 in the first embodiment are not shown in FIG. 6, it does not mean that those elements are excluded in the second embodiment. In the system according to the second embodiment, elements having the same reference numerals and names as those of the first embodiment have the same configurations and actions as those of the first embodiment unless otherwise specified in the following.

The position transducer 22 includes, as shown in FIG. 6, the magnetic field intensity/direction detectors $23a$ to $23h$, fixing members $7a$ and $7b$ for fixing the magnetic field intensity/direction detectors $23a$ to $23h$ to the subject 1, receiving antennas $A_1$ to $A_n$ for receiving radio signals transmitted from the capsule endoscope 21, and a position processor 24 for processing the information obtained by the magnetic filed intensity/direction detector $23a$ to $23h$ and the receiving antennas $A_1$ to $A_n$ and deriving information of the position in the subject 1, of the capsule endoscope 21.

The magnetic field intensity/magnetic field direction detectors $23a$ to $23h$ are for detecting magnetic field intensities and magnetic field directions in positions in which they are located, respectively. Specifically, the magnetic field intensity/magnetic field direction detectors $23a$ to $23h$ are formed by MI sensors or the like with functions of detecting magnetic field intensity and magnetic field direction. In the first embodiment, only the magnetic field intensity output from the device in the subject is detected, whereas, in the second embodiment, not only the position of the device (capsule endoscope 21) but also the orientation direction thereof is detected, in other words, not only the magnetic field intensity but also the magnetic field direction is detected.

The receiving antennas $A_1$ to $A_n$ are to receive radio signals transmitted from the capsule endoscope 21. As is explained later, the capsule endoscope 21 in the second embodiment has the function of capturing an image of the inside of the subject 1 and transmitting the image to the outside by radio. The receiving antennas $A_1$ to $A_n$ have the configuration of receiving a radio signal transmitted from the capsule endoscope 21 and outputting it to the position processor 24. The receiving antennas $A_1$ to $A_n$ are constructed by, concretely, for example, a loop antenna and a fixing unit that fixes the loop antenna to the subject 1. When radio signals are transmitted from the capsule endoscope 21, the radio signals may be received by all of the receiving antennas $A_1$ to $A_n$. However, in the second embodiment, the radio signal is received by using a receiving antenna that is determined to be most adapted to reception by an antenna selector 46 that is explained later among the plurality of receiving antennas $A_1$ to $A_n$.

Figure 7:
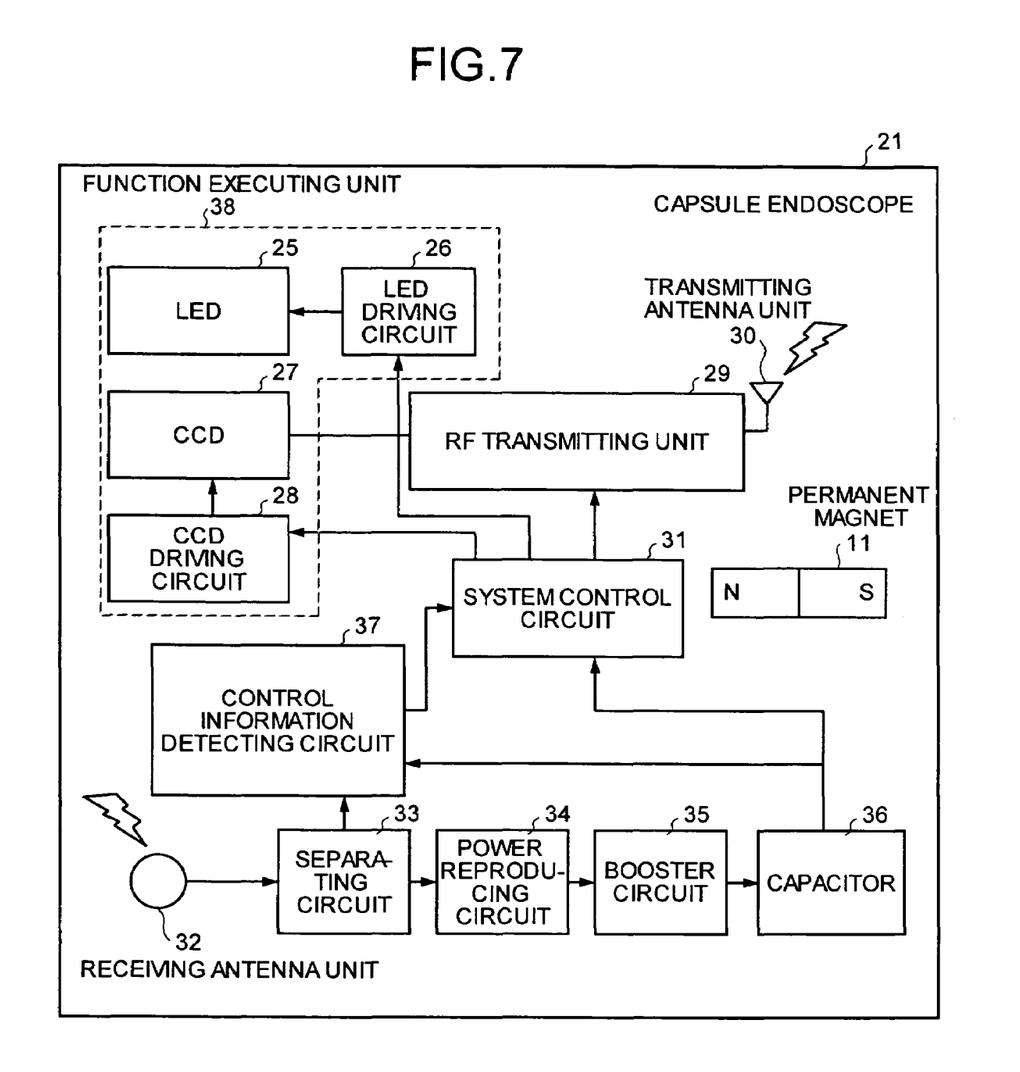
FIG. 7 is a schematic view of the capsule endoscope as a component of the system according to the second embodiment.

FIG. 7 is a block diagram of the capsule endoscope 21. The capsule endoscope 21 has, like the test capsule 2 in the first embodiment, the permanent magnet 11 as the magnetic field generator. Further, the capsule endoscope 21 includes a light emitting diode (LED) 25 functioning as a illuminating unit that illuminates an image capturing region at the time of capturing an image of the inside of the subject 1; an LED driving circuit 26 that controls a driving state of the LED 25; a charge-coupled device (CCD) 27 functioning as an image capturing unit for capturing a reflection light image from the region illuminated by the LED 25; and a CCD driving circuit 28 that controls a driving state of the CCD 27. The LED 25, LED driving circuit 26, CCD 27, and CCD driving circuit 28 are defined as a function executing unit 38 having a predetermined function as a whole.

The capsule endoscope 21 includes an RF transmitting unit 29 that modulates image data captured by the CCD 27, thereby generating an RF signal; a transmitting antenna unit 30 as a radio unit for transmitting the RF signal output from the RF transmitting unit 29 by radio; and a system control circuit 31 for controlling the operation of the LED driving circuit 26, CCD driving circuit 28, and RF transmitting unit 29.

By having the mechanisms, the capsule endoscope 21 obtains image data of a region to be tested that is illuminated by the LED 25 by the CCD 27 while the capsule endoscope 21 is introduced in the subject 1. The captured image data is converted to an RF signal by the RF transmitting unit 29 and, after that, the RF signal is transmitted to the outside via the transmitting antenna unit 30.

The capsule endoscope 21 also includes a receiving antenna unit 32 for receiving a radio signal sent from the position transducer 22 side; and a separating circuit 33 for separating the power supply signal from the signal received by the receiving antenna unit 32. The capsule endoscope 21 also includes a power reproducing circuit 34 for reproducing power from the separated power supply signal; a booster circuit 35 for boosting the reproduced power; and a capacitor 36 for storing the boosted power. The capsule endoscope 21 also includes a control information detecting circuit 37 for detecting a control information signal from the components separated from the power supply signal by the separating circuit 33 and outputting the detected control information signal to the system control circuit 31. The system control circuit 31 also includes the function of distributing drive power supplied from the capacitor 36 to the other elements.

By having the mechanisms, first, the capsule endoscope 21 receives the radio signal sent from the position transducer 22 side by the receiving antenna unit 32 and separates the power supply signal and the control information signal from the received radio signal by the separating circuit 33. The control information signal separated by the separating circuit 33 is output to the system control circuit 31 via the control information detecting circuit 37 and used for driving and controlling the LED 25, CCD 27, and RF transmitting unit 29. On the other hand, the power supply signal is reproduced as power by the power reproducing circuit 34. The potential of the reproduced power is boosted to potential adapted to the capacitor 36 by the booster circuit 35, and the boosted potential is stored in the capacitor 36.

Figure 8:
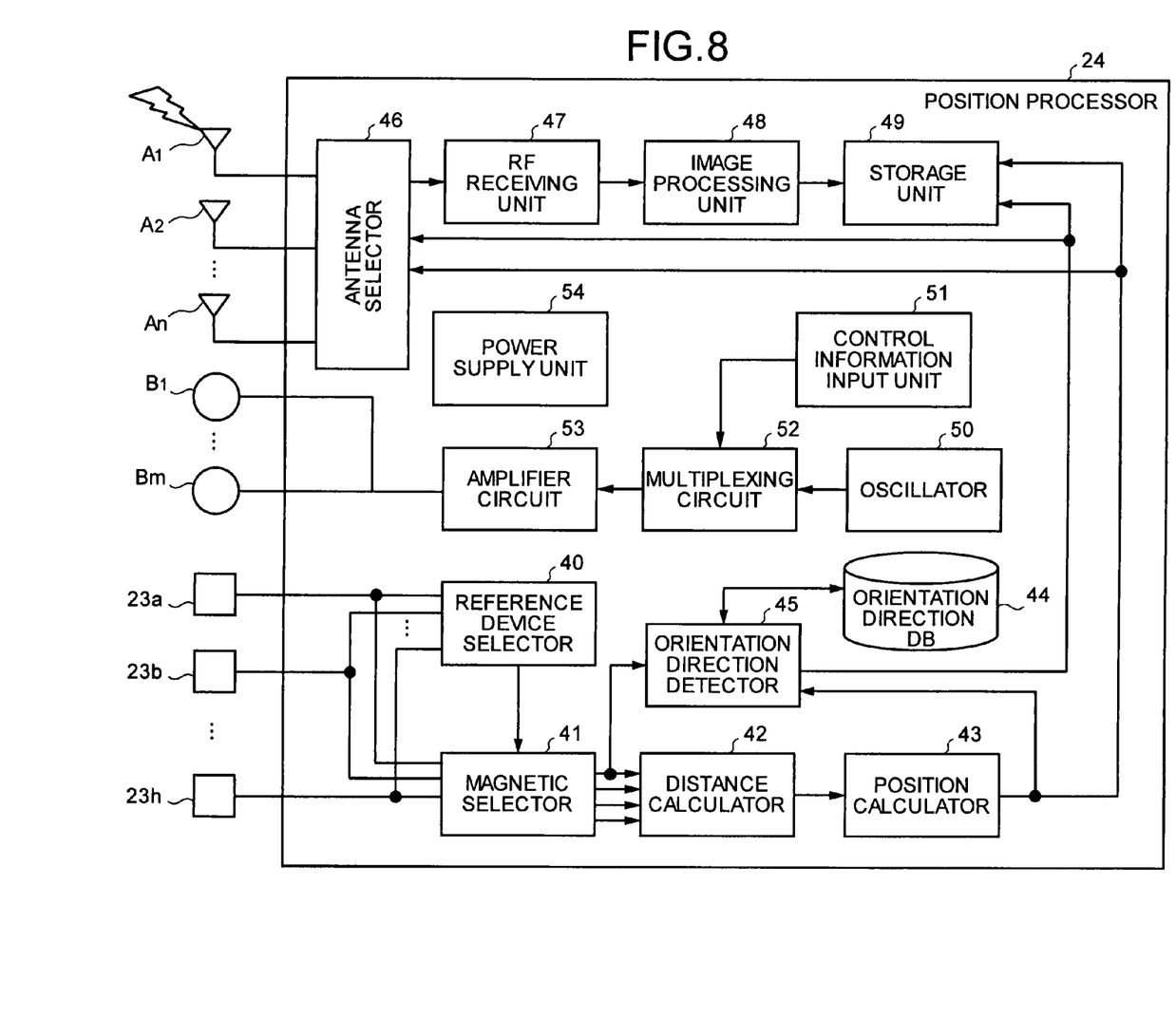
FIG. 8 is a schematic view of a position processor as a component of the system according to the second embodiment.

The configuration of the position processor 24 is explained. FIG. 8 is a block diagram of the position processor 24. The position processor 24 in the second embodiment has, as elements for detecting the position in the subject 1 of the capsule endoscope 21, the reference device selector 40, magnetic selector 41, distance calculator 42, and position calculator 43. In the second embodiment, the magnetic field intensity/magnetic field direction detectors 23a to 23h output not only the magnetic field intensity but also the magnetic field direction to the position processor 24, so that the second embodiment is different from the first embodiment with respect to the following points. The reference device selector 40 extracts the magnetic field intensity from the information output from the magnetic detectors 23a to 23h to select a reference device, and the distance calculator 42 has the function of deriving distance by extracting the magnetic field intensities received by the reference device and the selected devices from the information input from the magnetic selector 41. The operation of detecting the position of the capsule endoscope 21 in the second embodiment is almost the same as that in the first embodiment and its detailed description will not be repeated.

Furthermore, the position processor 24 includes an orientation direction database 44 used when detecting the orientation direction of the capsule endoscope 21 as described below, and an orientation direction detector 45 that detects the orientation direction of the capsule endoscope 21 based on the magnetic field direction at a predetermined magnetic field intensity/magnetic field direction detector 23 output from the magnetic selector 41. The orientation direction database 44 stores in advance data on magnetic field intensity received at the magnetic field intensity/magnetic field direction detector 23 and orientation directions relative to the positional relation between the magnetic field intensity/magnetic field direction detectors 23 and the capsule endoscope 21. The specific operation of the orientation direction database 44 and orientation direction detector 45 will be described later in detail.

The position processor 24 also includes the function of a receiving apparatus for receiving image data of the inside of the subject 1, which is sent from the capsule endoscope 21 by radio. Concretely, the position processor 24 has: the antenna selector 46 for selecting an antenna used for data reception from the receiving antennas $A_1$ to $A_n$; an RF receiving unit 47 that performs a predetermined process such as demodulation on a radio signal received by the selected receiving antenna, extracts image data captured by the capsule endoscope 21 from the radio signal, and outputs the extracted image data; an image processing unit 48 for performing a necessary process on the output image data; and a storage unit 49 for storing the processed image data.

The antenna selector 46 selects the receiving antenna that is most adapted to receive the radio signal transmitted from the capsule endoscope 21. Concretely, the antenna selector 46 grasps the positions of the receiving antennas $A_1$ to $A_n$ in advance and receives information of the position of the capsule endoscope 21 derived by the position calculator 43 and information of the orientation direction of the capsule endoscope 21 derived by the orientation direction detector 45. The antenna selector 46 has the function of selecting a receiving antenna that is estimated to have the most excellent reception sensitivity based on the position and the orientation direction of the capsule endoscope 21 and outputting a radio signal received by the selected receiving antenna to the RF receiving unit 47.

The storage unit 49 has the function of storing image data output from the image processing unit 48 and the position and the orientation direction of the capsule endoscope 21 at the time point the output image data is captured in a state where the image data and the position of the capsule endoscope 21 are associated with each other. The position processor 24 has the configuration of outputting the information obtained by the position calculator 43, orientation direction detector 45, and the image processing unit 48 to the storage unit 49 as also shown in FIG. 8, and the storage unit 49 has the function of storing the information in the associated state. As a result, in the storage unit 49, the image data of a predetermined region in the subject 1 and the position and the orientation direction of the capsule endoscope 21 at the time point the image data is captured is stored in a state where the image data and the position and the orientation direction of the capsule endoscope 21 are associated with each other.

The position processor 24 also has the function of generating a power supply signal and the like transmitted to the capsule endoscope 21 and outputting the power supply signal to the power supply antennas $B_1$ to $B_m$. Concretely, the position processor 24 includes an oscillator 50 having the function of generating a power supply signal and the function of specifying an oscillation frequency; a control information input unit 51 that generates a control information signal for controlling the drive state of the capsule endoscope 40; a multiplexing circuit 52 for combining the power supply signal and the control information signal; and an amplifier circuit 53 for amplifying the intensity of the combined signal. The signal amplified by the amplifier circuit 53 is sent to the power supply antennas $B_1$ to $B_m$ and transmitted to the capsule endoscope 21. The position processor 24 includes a power supply unit 54 having a predetermined storage, an AC power adapter, or the like, and the elements of the position processor 24 uses the power supplied from the power supply unit 54 as driving energy.

Next, in the system for detecting a position within a subject according to the second embodiment, the significance of detection of the orientation direction of the capsule endoscope 21 and the operation of detecting the orientation direction will be described. As described above, in the system for detecting a position in a subject according to the second embodiment, the capsule endoscope 21 includes a predetermined function executing unit and the information acquired by the function executing unit is wirelessly transmitted to the position transducer 22 side. Accordingly, the position transducer 22 includes plural receiving antennas $A_1$ to $A_n$ for receiving transmitted radio signals and antenna selector 46 selects a receiving antenna most suitable for reception from the plural receiving antennas $A_1$ to $A_n$.

As an algorithm of selecting a receiving antenna most suitable for reception from the plural receiving antennas $A_1$ to $A_n$, first, determination according to the positional relation with the capsule endoscope 21 can be cited. For example, it is conceivable that, on the assumption that the radio signal transmitted from the capsule endoscope 21 are attenuated according to the distance, the position of the capsule endoscope 21 is derived by a position detection mechanism same as in the first embodiment, and the receiving antenna nearest to the derived position is used.

However, when the radio signals from the capsule endoscope are received, selecting the receiving antenna according to only the positional relation with the antenna is not necessarily appropriate. That is, the transmitting antenna unit 30 used for radio transmission from the capsule endoscope 21 does not transmit the radio signals toward various directions with uniform intensity, but transmits the radio signals with a certain degree of directivity because the unit is formed by a loop antenna or the like, for example. Therefore, it is preferred that the receiving antenna most suitable for receiving the radio signals transmitted from the capsule endoscope is not determined according to only the positional relation with the capsule endoscope, but determined in consideration of the directivity of the radio signals transmitted from the transmitting antenna unit 30. Further, since the transmitting antenna unit 30 is fixed within the capsule endoscope 21, it is important to grasp the orientation direction of the capsule endoscope 21 within the subject 1 to detect the orientation direction of the transmitted radio signals. According to such circumstances, in the second embodiment, the orientation direction of the capsule endoscope 21 is detected with not only the mechanism of detecting the position of the capsule endoscope 21 within the subject 1 as in the first embodiment, but with the orientation direction database 44 and the orientation direction detector 45.

Figure 9:
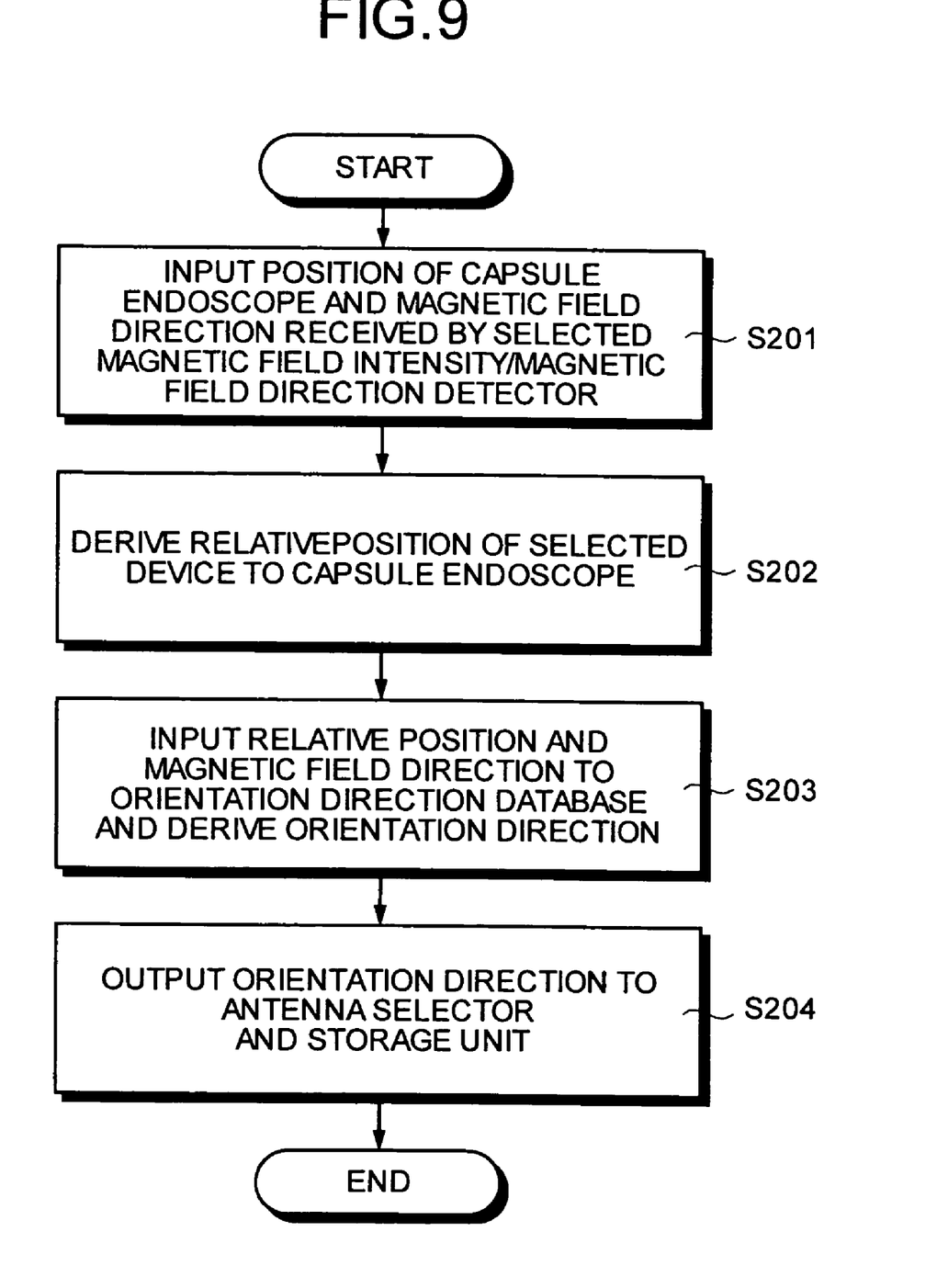
FIG. 9 is a flowchart of operations of the position processor.
Figure 10:
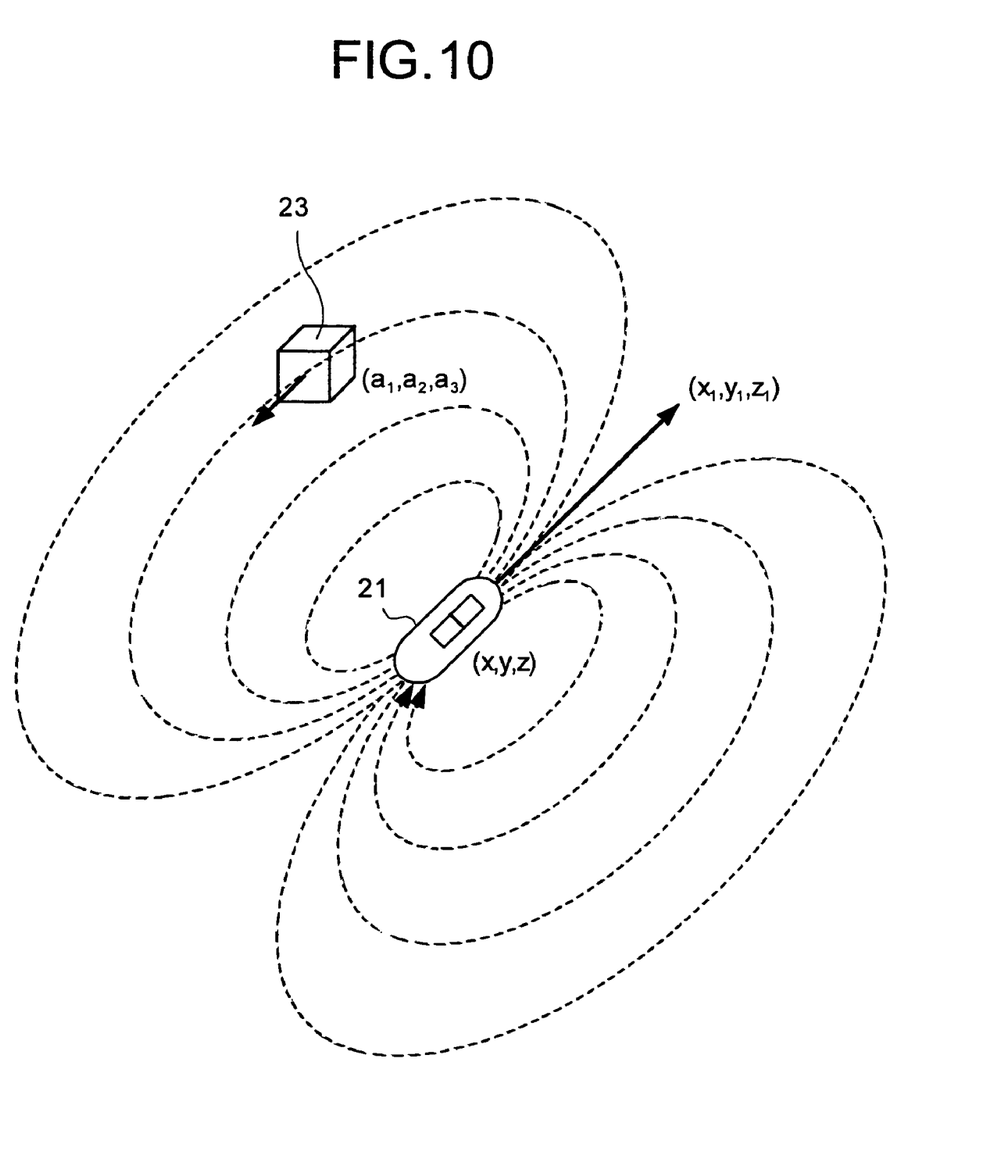
FIG. 10 is a schematic view of calculating the orientation direction of the test capsule by the position processor.

FIG. 9 is a flowchart for explanation of the detection operation of the orientation direction of the capsule endoscope 21 in the orientation direction detector 45 in the second embodiment. Further, FIG. 10 is a diagram that depicts the relation between the orientation direction of the capsule endoscope and the magnetic field intensity/magnetic field direction detector 23. As below, the operation of the orientation direction detector 45 will be described with reference to FIGS. 9 and 10 as necessary.

First, the orientation direction detector 45 inputs the position of the capsule endoscope 21 and magnetic field direction received by the magnetic field intensity/magnetic field direction detector 23 selected from the magnetic field intensity/magnetic field direction detectors 23a to 23h (step S201). Any selection algorithm may be used for the selection of the magnetic field intensity/magnetic field direction detector 23, and in the second embodiment, the magnetic field intensity/magnetic field direction detector 23 with the largest received magnetic field intensity is selected as an example. In the example of FIG. 10, the orientation direction detector 45 grasps the coordinates $(a_1,a_2,a_3)$ of the selected magnetic field intensity/magnetic field direction detector 23 and the magnetic field direction represented by the direction vector shown by an arrow.

Then, the orientation direction detector 45 calculates the relative position of the magnetic field intensity/magnetic field direction detector 23 selected at step S201 to the capsule endoscope 21 (step S202). Specifically, the position of the capsule endoscope 21 calculated by the position calculator 43 is input to the orientation direction detector 45, and the unit 45 derives the relative coordinates of the magnetic field intensity/magnetic field direction detector 23 selected at step S201 to the capsule endoscope 21. In the example of FIG. 10, the relative position coordinates $(a_1\text{-}x,a_2\text{-}y,a_3\text{-}z)$ of the magnetic field intensity/magnetic field direction detector 23 with the position of the capsule endoscope 21 as a point of origin are derived based on the coordinates $(a_1,a_2,a_3)$ of the magnetic field intensity/magnetic field direction detector 23 and the coordinates $(x,y,z)$ of the capsule endoscope 21.

Then, the orientation direction detector 45 inputs the magnetic field direction input at step S201 and the relative position of the magnetic field intensity/magnetic field direction detector 23 selected at step S202 to the orientation direction database 44 and acquires data on the orientation direction of the capsule endoscope 21 (step S203). As shown in FIG. 10, since the direction of the constant magnetic field output from the permanent magnet 11 provided within the capsule endoscope 21 has a nature which is uniquely determined depending on the orientation direction of the capsule endoscope 21 and the position relative to the capsule endoscope 21, in the orientation direction database 44, the orientation direction of the capsule endoscope 21, the relative coordinates to the capsule endoscope 21, and the directions of the constant magnetic field in the relative coordinates are stored in advance in an associated condition. Accordingly, with the input of the relative coordinates of the magnetic field intensity/magnetic field direction detector 23 and the detected direction of the constant magnetic field to the orientation direction database 44, the orientation direction of the capsule endoscope 21 can be extracted. In the example in FIG. 10, the orientation direction of the capsule endoscope 21 is derived as $(x_1,y_1,z_1)$ based on the output result from the orientation direction database 44.

Finally, the orientation direction detector 45 outputs the acquired data on the orientation direction of the capsule endoscope 21 to the antenna selector 46 and the storage unit 49 (step S204). The antenna selector 46 selects the receiving antenna most suitable for reception based on the data on the orientation direction and the information on the position output from the position calculator 43, and the storage unit 49 stores the orientation direction of the capsule endoscope 21 at a predetermined time in association with the image data and the position information of the capsule endoscope 21.

The advantages of the system according to the second embodiment is explained. First, in the system according to the second embodiment, in a manner similar to the first embodiment, the capsule endoscope 21 includes therein the permanent magnet 11 and the position of the capsule endoscope 21 is detected based on the constant magnetic field output from the permanent magnet 11. As already mentioned above, the constant magnetic field has a characteristic that it attenuates almost unconditionally irrespective of the values such as dielectric constant, magnetic permeability, and the like in organs and the like in the subject 1. Consequently, there is an advantage such that the position of the capsule endoscope 21 can be accurately detected more than the case of performing position detection by using a radio signal.

Further, the system according to the second embodiment has a configuration that the orientation direction of the capsule endoscope 21 is detected based on the constant magnetic field output from the permanent magnet 11. Similarly to the position detection, the constant magnetic field output from the permanent magnet 11 is hardly affected by the component material within the subject 1 and has a property that the magnetic field direction in the predetermined position is nearly uniquely determined based on the orientation direction of the capsule endoscope 21 and the relative position to the capsule endoscope 21. Therefore, when the distribution of orientation of the constant magnetic field output by the permanent magnet 11 is obtained in advance to be stored in the orientation direction database 44, with the reference to the orientation direction database 44 based on the information obtained via magnetic field intensity/magnetic field direction detector 23, the orientation direction of the capsule endoscope 21 can be detected accurately.

Furthermore, since the system according to the second embodiment has the configuration that the orientation direction of the capsule endoscope 21 is detected based on the constant magnetic field similarly to the position detection, the system has an advantage of simple configuration. That is, the system according to the second embodiment does not require addition of new components within the capsule endoscope 21 for realizing the function of detecting the orientation direction of the capsule endos cope 21, whereby the compact and low-cost system can be realized.

The system for detecting a position in a subject according to the second embodiment has a configuration that the antenna selector 46 selects the receiving antenna based on the position and the orientation direction of the derived capsule endoscope 21. The reception sensitivity of the radio signal in the receiving antenna depends on the distance from the capsule endoscope 21 and the orientation of the transmitting antenna unit 30 in the capsule endoscope 21. Therefore, a receiving antenna to be used can be accurately selected based on the position and the orientation direction of the capsule endoscope 21, and a position information detecting system capable of receiving a radio signal transmitted from the capsule endoscope 21 always at high sensitivity can be realized.

Further, the system according to the second embodiment has a configuration of outputting image data of the inside of the subject 1 captured and the derived position and the orientation direction of the capsule endoscope 21 to the storage unit 49. Therefore, image data obtained by the capsule endoscope 21 and the derived position and the orientation direction at the time of image capture of the capsule endoscope 21 can be stored so as to be associated with each other. At the time of displaying image data on the display 4, only the image data positioned in a predetermined range can be designated to be displayed. In other words, every image data is not displayed on the display 4 but image data of a region of interest of the user, for example, image data of only the small intestine can be displayed on the display 4. Thus, the position information detecting system that is convenient to doctors and the like can be realized.

Although the invention has been described above by the first and second embodiments, the invention is not limited to the foregoing embodiments and various embodiments, modifications, and application examples can be made by those skilled in the art. For example, the system according to the first embodiment may have a configuration where the orientation direction of the test capsule 2 is derived as in the second embodiment.

Further, though in the first and the second embodiments, a plurality of magnetic detectors 6 and magnetic field intensity/magnetic field direction detectors 23 are each disposed on an outer surface of the subject 1 as to detect an apex of the cube, the disposition of the detectors is not limited to such. With respect to the magnetic detectors 6 and the like, it is sufficient to grasp relative positions to the subject 1 in advance. By using the relative positions, position and orientation direction detection is possible without disposing the magnetic detectors 6 in a cube shape. The number of the magnetic detectors 6 and the like is not limited to eight. As the simplest configuration, a system using a single magnetic detector 6 or the like can be constructed. Specifically, the test capsule 2 or the capsule endoscope 21 as the device to be introduced in the subject does not travel arbitrarily in the subject 1 but travels along a path that is determined to a certain degree of predetermined organs such as esophagus, stomach, small intestine, large intestine, and the like. Therefore, it is possible to preliminarily grasp a travel path of the device to be introduced in a subject to a certain degree. The position of the device to be introduced in a subject can be detected by using the path information grasped in advance and the intensity of the constant magnetic field received by the single magnetic detector.

Further, in the first and second embodiments, the reference device and the selected devices are selected by using the reference device selector 14 (or 40) and the magnetic selector 15 (or 41), and position detection is made based on the magnetic field intensities detected by the reference device and the selected devices. The configuration, however, is not essential to the invention. For example, it is also possible to derive the distance from the test capsule 2 or capsule endoscope 21 based on detected intensities with respect to all of the magnetic detectors 6$a$ to 6$h$ and generate eight ways of equations similar to Equations (2) to (5) to derive the position of the test capsule 2 or the like. In the case of the configuration, computation using, for example, the least square method is possible. Thus, there is an advantage such that an error of derivation of the position of the test capsule 2 or the like can be further reduced.

Similarly, in the second embodiment, for example, the orientation direction of the capsule endoscope 21 may be derived via the plural magnetic field intensity/magnetic field direction detectors 23. That is, it is also preferable to derive the orientation direction at the plural magnetic field intensity/magnetic field direction detectors 23 by the above described method and to find the average of the derived orientation directions, to realize more accurate derivation of the orientation direction. Same applies to the detection of the position of the device, for which a plurality of position detections may be performed with the magnetic field intensity detector 6 or the like, and the average of the obtained positions may be found.

Although the function executing unit 38 having the CCD 27 and the like as an image capturing unit and the LED 25 and the like as an illuminating unit has been described in the second embodiment, the function executing unit 38 may obtain, in addition to the above, information of pH and the temperature in the subject 1. A configuration that the device to be introduced in a subject has an oscillator to capture an ultrasonic image of the inside of the subject 1 may be also employed. Further, a plurality of pieces of information may be obtained from the information of the inside of the subject.

The radio signal output from the power supply antennas $B_1$ to $B_m$ is not always limited to a signal obtained by multiplexing the control information signal and the power supply signal. Further, radio transmission from the position transducer to the capsule endoscope may not be performed. The power supply signal and a signal other than the control information signal may be multiplexed and the resultant signal may be transmitted. The position transducer 22 may receive only the radio signal output from the capsule endoscope. It is also possible to provide a storage unit in the capsule endoscope and, after the capsule endoscope is excreted to the outside of the subject, read information from the storage unit.

Further, in the second embodiment, the selection of the power supply antennas $B_1$ to $B_m$ has not been referred to particularly, however, as with the receiving antennas $A_1$ to $A_n$, the most suitable one may be selected based on the position and orientation direction of the capsule endoscope 21 to perform radio transmission. That is, in order to improve the supply efficiency of power supply signals or the like, not the transmission of radio signals uniformly from all of the power supply antennas, but selection of an antenna in response to the orientation direction or the like of the receiving antenna unit 32 provided within the capsule endoscope 21 can be performed using the orientation direction or the like of the capsule endoscope 21.

As is clear from the foregoing, the system according to the present invention is useful in connection with the swallowable capsule endoscope employed for the medical treatment, and particularly suitable for a device to be introduced into a subject, such as a patient, for the position detection.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A system comprising:
   a device that is swallowed and passes through a subject;
   a magnetic field generator generating a constant magnetic field and disposed in the device;
   a position transducer that includes a plurality of magnetic detectors, adapted to be disposed in fixed positions forming the vertexes of a cube relative to the subject outside the subject and detecting intensities of the constant magnetic field generated by the magnetic field generator;
   a reference device selector that selects one magnetic detector out of the plurality of magnetic detectors as a reference magnetic detector based on the detected intensities;
   a selector that selects specific magnetic detectors based on a selection result of the reference device selector; and
   a position processor calculating a position of the device in the subject based on a detection result of the specific magnetic detectors;
   wherein the specific magnetic detectors includes three magnetic detectors which are selected from the plurality of magnetic detectors disposed on axes orthogonal to one another at the reference magnetic detector.

2. The system according to claim 1, wherein
   the position processor calculates a distance between the device and each of the magnetic detectors based on intensities of magnetic field components detected by the magnetic detectors, and calculates a position of the device in the subject based on the calculated distances.

3. The system according to claim 1 wherein the magnetic field generator is disposed in a position where a direction of the constant magnetic is fixed, and
   the position transducer further includes a magnetic field direction detector detecting the direction of the constant magnetic field, and an orientation direction detector detecting an orientation direction of the device in the subject based on the direction detected by the magnetic field direction detector.

4. The system according to claim 3 wherein the position transducer further includes an orientation direction database that stores, in advance, a distance from the magnetic field generator, a relation between a direction of the constant magnetic field, and an orientation direction of the device in the subject, and
   the orientation direction detector detects the orientation direction of the device in the subject using the orientation direction database.

5. The system according to claim 1, wherein the device further includes
   a predetermined function executing unit that obtains information of an inside of the subject; and
   a radio transmitting unit that transmits the information of the inside of the subject with radio communication, and
   the position transducer further includes a receiving unit that receives a radio signal transmitted from the radio transmitting unit.

6. The system according to claim 5, wherein the magnetic field generator is disposed in a position where a direction of the constant magnetic is fixed,
   the position transducer further includes
   a magnetic field direction detector detecting the direction of the constant magnetic field,
   an orientation direction detector detecting an orientation direction of the device in the subject based on the direction detected by the magnetic field direction detector,
   a plurality of receiving units each receiving a radio signal transmitted from the radio transmitting unit, and
   a selector that selects a receiving unit used for receiving the radio signal based on the position calculated by the position processor and the orientation direction detected by the orientation direction detector.

7. The system according to claim 6, wherein the magnetic field generator is a magnet.

8. The system according to claim 6, wherein the magnetic field generator is a coil.

9. The system according to claim 8, wherein the constant magnetic field is generated by applying constant electric current to the coil.

10. The system according to claim 6, wherein the selector selects a antenna for receiving the radio signal according to a result obtained in the position transducer.

11. The system according to claim 10, wherein the obtained result is a position information of the device.

12. The system according to claim 10, wherein the obtained result is an orientation information of the device.

13. The system according to claim 10, wherein the selector includes an antenna selector that obtains a position of an antenna, based on the supplied information from the position processor determining a position of the device and from the orientation direction detector detecting an orientation direction of the device, to estimate and select an antenna which receives a strongest signal.

14. The system according to claim 10, wherein the antenna selector selects an antenna which is nearest to the reference device selected by the reference device selector.

15. The system according to claim 6, further comprising a storage unit that stores image data associated with a position and an orientation data of the device, wherein the system displays only image data captured when the device is located within a specific area according to data stored in the storage unit.

16. The system according to claim 5, wherein the function executing unit includes
- an illuminating unit that illuminates an inside of the subject; and
- an image capturing unit that captures an image of a region illuminated by the illuminating unit.

17. The system according to claim 16, wherein the position transducer further includes a storage unit that stores an image captured by the image capturing unit and the position of the device at when the image is captured, so that the image and the position are associated with each other.

18. A method used for the system of claim 5, comprising the steps of:
- detecting a magnetic field which is generated by a magnet field generator by using a magnetic detector;
- obtaining a relative distance between the magnetic detector and the device;
- calculating at least either of a position or an orientation of the device;
- correcting coordinates on which the device exists; and
- repeating the steps of detecting, obtaining, calculating, and correcting to compute a traveling route of the device.

19. A method according to claim 18, further comprising the steps of:
- storing the position data in a portable recording medium; and
- connecting the portable recording medium to a display.

20. The system according to claim 1, wherein the device is a capsule endoscope.

21. The system according to claim 1, wherein the device is a test capsule that conducts a preliminary survey to predict how the device moves inside the subject.

22. The system according to claim 21, wherein a housing of the device is made from a material that is broken down by the body.

23. The system according to claim 22, wherein the magnetic field generator is disposed in the housing.

24. The system according to claim 21, wherein the magnetic field generator is a magnet.

25. The system according to claim 21, wherein the magnetic field generator is a coil.

26. The system according to claim 25, wherein the constant magnetic field is generated by applying constant electric current to the coil.

27. The system according to claim 26, wherein the position transducer includes a database of orientation of the device.

28. The system according to claim 21, wherein the position transducer includes a portable record medium that stores a traveling route of the device and is disposed in the position transducer.

29. The system according to claim 28, further comprising a display unit that links with the portable record medium and displays the moving route of the device in the subject.

30. A method for determining a position of a device in a subject, the method comprising the steps of:
- introducing a first device inside the subject;
- detecting a first magnetic field which is generated by a magnet field generator disposed in the first device by using a plurality of magnetic detectors which are disposed to form the vertexes of a cube;
- tracking a traveling route of the device by obtaining a position of the device by using a plurality of magnetic field intensities detected by the plurality of magnetic detectors;
- introducing a second device inside the subject;
- detecting a second magnetic field which is generated by a second magnet field generator disposed in the second device by using the plurality of magnetic detectors; and
- obtaining a position information of the second device by using the traveling route obtained by the step of tracking and the magnet field intensity detected by the step of detecting the second magnetic field;
- wherein the detecting step includes selecting one magnetic sensor out of the plurality of magnetic detectors as a reference magnetic detector based on the detected intensities, and selecting as specific magnetic detectors three magnetic detectors which are selected from the plurality of magnetic detectors disposed on axes orthogonal to one another at the reference magnetic detectors, based on a selection result of the reference device selector.

31. A method for determining a position of a device that is swallowed and passes through a subject, the method comprising the steps of:
- disposing a plurality of magnetic detectors to form the vertexes of a cube;
- detecting a magnetic field which is generated by a magnet field generator by using the plurality of magnetic detectors;
- obtaining a relative distance between the plurality of magnetic detectors and the device;
- calculating at least either of a position or an orientation of the device;
- correcting coordinates on which the device exists; and
- repeating the steps of detecting, obtaining, calculating, and correcting to compute a traveling route of the device;
- wherein the detecting step includes selecting one magnetic sensor out of the plurality of magnetic detectors as a reference magnetic detector based on the detected intensities, and selecting as specific magnetic detectors three magnetic detectors which are selected from the plurality of magnetic detectors disposed on axes orthogonal to one another at the reference magnetic detector, based on a selection result of the reference device selector.

32. A method according to claim 31, further comprising the steps of:
- storing an image data associated with a position and an orientation data of the device in a storage unit; and
- displaying only an image data captured when the device is located within a specific area according to a data stored in the storage unit.

33. A method according to claim 31, further comprising the steps of:
- storing the position data in a portable recording medium; and
- connecting the portable recording medium to a display.

* * * * *